United States Patent
Aoyagi et al.

(10) Patent No.: US 6,671,526 B1
(45) Date of Patent: *Dec. 30, 2003

(54) PROBE AND APPARATUS FOR DETERMINING CONCENTRATION OF LIGHT-ABSORBING MATERIALS IN LIVING TISSUE

(75) Inventors: Takuo Aoyagi, Tokyo (JP); Masayoshi Fuse, Tokyo (JP); Sunao Takeda, Tokyo (JP); Cheng-tai Xie, Tokyo (JP); Michio Kanemoto, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 171 days.

This patent is subject to a terminal disclaimer.

(21) Appl. No.: 09/692,044

(22) Filed: Oct. 20, 2000

Related U.S. Application Data

(63) Continuation-in-part of application No. 09/356,521, filed on Jul. 19, 1999, now Pat. No. 6,230,035.

(30) Foreign Application Priority Data

| Jul. 17, 1998 | (JP) | 10-203388 |
| Mar. 11, 1999 | (JP) | 11-65489 |
| Nov. 11, 1999 | (JP) | 11-320912 |
| Sep. 27, 2000 | (JP) | 2000-293951 |

(51) Int. Cl.[7] .................................. A61B 5/00
(52) U.S. Cl. ........................ 600/310; 600/322
(58) Field of Search ........................ 600/310, 311, 600/336, 323, 322, 316, 324, 473, 476

(56) References Cited

U.S. PATENT DOCUMENTS

| 5,690,104 A | * | 11/1997 | Kanemoto et al. | 600/323 |
| 5,782,757 A | * | 7/1998 | Diab et al. | 600/323 |
| 6,041,247 A | * | 3/2000 | Weckstrom et al. | 600/323 |
| 6,230,035 B1 | * | 5/2001 | Aoyagi et al. | 600/310 |

FOREIGN PATENT DOCUMENTS

| JP | 53-26437 | 8/1978 | A61B/5/00 |

OTHER PUBLICATIONS

Bio Medical Engineering (Oct. 1999) Medical Electronics and Biological engineering.

Shibata, Kazuo, *Spectrophotometry of Translucent Biological Materials—Opal Glass Transmission Method*, Methods of Biochemical Analysis, vol. VII, Intersc. New York, 1959.

\* cited by examiner

*Primary Examiner*—Eric F. Winakur
*Assistant Examiner*—David J. McCrosky
(74) *Attorney, Agent, or Firm*—Sughrue Mion, PLLC

(57) ABSTRACT

A probe 1 includes a light irradiating device 2 and a light receiving device 3, which are oppositely disposed sandwiching living tissue 10. The light irradiating device 2 includes a light source 5 and a scattering plate 6 located in front of the light source 5. The light receiving device 3 includes a photo diode 8 and a light scattering portion. With such an arrangement, of the attenuation of the living tissue 10, non-absorbing attenuation is free from the wavelength. A ratio of absorbing attenuation and a thickness of a blood layer is not affected by a thickness of living tissue. Further, the absorbing attenuation is not dependent on a depth of the blood layer.

12 Claims, 15 Drawing Sheets

PROBE AND APPARATUS FOR DETERMINING CONCENTRATION OF LIGHT-ABSORBING MATERIALS IN LIVING TISSUE

This is a Continuation-In-Part Application of Ser. No. 09/356,521 filed on Jul. 19, 1999, now U.S. Pat. No. 6,230,035.

BACKGROUND OF INVENTION

1. Field of the Invention

The present invention relates to a method of continuously and noninvasively determining a ratio of concentrations of a plurality of light-absorbing materials in blood, particularly in arterial blood, of a living tissue. This method is used mainly in the medical field.

2. Related Art

The principle of this kind of technique is called a pulse photometry. The pulse photometry will briefly be described hereunder.

Arterial blood is present in living tissue. An amount of the arterial blood in the tissue periodically varies with periodic contraction of the heart. Accordingly, when light of a constant intensity is irradiated into living tissue, light transmitted through the living tissue periodically varies in intensity in a pulsation. The amplitude of a pulsation waveform of the light intensity variation reflects a light absorbing characteristic Of each of a plurality of components contained in the arterial blood.

Therefore, a ratio of concentrations of a plurality of light-absorbing materials in the arterial blood is able to be obtained in a manner that a plurality of light rays of proper wavelengths are irradiated into living tissue and lights transmitted through are measured, and the measured values are appropriately processed. This is the principle of the photometry.

This kind of the concentration-ratio measuring method was first described in Japanese patent Unexamined Japanese Patent Publication Sho 50-128387. Two specific applications of the technique are described in the specification of the patent.

One of those applications is a method of continuously and noninvasively measuring an oxygen saturation of hemoglobin in arterial blood. This measuring method is called a pulse oximetry. An apparatus based on this method is called a pulse oximeter. The apparatus is widely used in the present medical field, and indispensably used, for example, in surgical operations on patients for securing their safety.

The other application is a method of measuring a dye dilution curve. In the measurement, dye is injected into a blood vessel of the human body, and a concentration of the dye in the arterial blood is noninvasively and continuously measured. By the measuring method, the cardiac output, circulatory blood volume, effective hepatic blood flow, and the like may easily be measured. An apparatus based on the measuring method is also put into practice, and commercially available.

The conventional applications of the pulse photometry are as stated above. Those applications have the following problems to be solved, however.

(1) Improvement of a level of measuring accuracy of the conventional apparatus:

With regard to the pulse oximeter, in the oxygen inhalation for a premature baby suffering from respiratory insufficiency, for example, it is required that a concentration of oxygen inhaled is as low as possible. However, the present pulse oximeter is insufficient in its measuring accuracy for adjusting a concentration of inhaled oxygen to a proper concentration value. With regard to the dye dilution curve measuring apparatus, its measuring accuracy must be high in order that a doctor quickly and accurately diagnoses in clinical diagnosis.

(2) To pursue the possibility of a variety of applications

In an example where a trace of carboxyhemoglobin or methemoglobin is contained in the arterial blood or when a trace of bilirubin is contained therein, it is important to noninvasively and accurately measure it. Such a measurement is impossible at the present stage, however. The measurement of the dye dilution curve is greatly affected by a variation of an oxygen saturation when some kind of dye is used Those problems must be solved. The number of wavelengths of lights must be increased to solve those problems.

So far as we know, there is no method of correctly carrying out the measurement in question by increasing the number of wavelengths method of lights, however. This is the problem of multiple wavelengths. The present invention presents a solution to this problem.

SUMMARY OF INVENTION

The present invention is made to present a solution to the multiple wavelength problem in the pulse photometry.

According to one aspect of the invention, there is provided a probe having a light irradiating device for irradiating light to living tissue and a light receiving device for receiving light from the living tissue, wherein the light irradiating device includes a light source for emitting a plurality of lights of different wavelengths, and a first light scattering portion located in front of the light source, and the light receiving device includes a photo-electric transducing portion for producing a signal based on an intensity of light received on a light sensitive surface, and a second light scattering portion.

According to another aspect of the invention, the light receiving device includes a light mixing portion provided between the living tissue and the light sensitive surface.

According to a third aspect of the invention, the light mixing portion includes a closed space a part of the inner wall of which includes the transmitted side surface of the second light scattering portion and the light sensitive surface.

According to a fourth aspect of the invention, the first light scattering portion consists of a light scattering plate.

According to a fifth aspect of the invention, the second light scattering potion includes a light scattering plate or a thing which scatters light by a light reflecting surface thereof.

According to a further aspect of the invention, there is provided an apparatus for determining concentrations of light-absorbing materials in living tissue, comprising: the probe; and concentration-ratio processing means for computing a ratio of concentrations of a plurality of light-absorbing materials in the living tissue based on an output signal of the photo-electric transducing portion of the probe.

According to an additional aspect of the invention, the concentration-ratio processing means obtains a variation of an optical attenuation of the living tissue based on a pulsating component of an output signal of the photo-electric transducing portion, and computes a ratio of concentrations of a plurality of light-absorbing materials based on the obtained attenuation variation.

According to another aspect of the invention, the concentration-ratio processing means includes attenuation variation component detecting means for obtaining attenuation variation components $\Delta A1, \Delta A2, \ldots, \Delta An$ of the respective wavelengths from variations of lights transmitted through or reflected by the living tissue when the living tissue is irradiated by the light irradiating device, variation component ratio detecting means for obtaining a ratio $\phi ij$ of each of an "m" number of combinations of two attenuation variation components ($\Delta Ai, \Delta Aj$) selected from an "n" number of attenuation variation components $\Delta A1, \Delta A2, \ldots, \Delta An$ obtained by the attenuation variation component detecting means, and computing means for computing at least one of an oxygen saturation and a ratio of concentrations of other light-absorbing materials in blood based upon an "m" number of simultaneous equations about the respective wavelengths and an "m" number of ratios $\phi ij$ obtained by the variation component ratio detecting means, on the assumption that the attenuation variation component is the sum of the attenuation variation components of absorbing attenuation and non-absorbing attenuation.

According to another aspect of the invention, the photoelectric transuding portion and the second light scattering portion are confronted from each other.

DETAILED DESCRIPTION OF PREFERRED EMBODIMENTS

Principle of Present Invention

Figure 1:
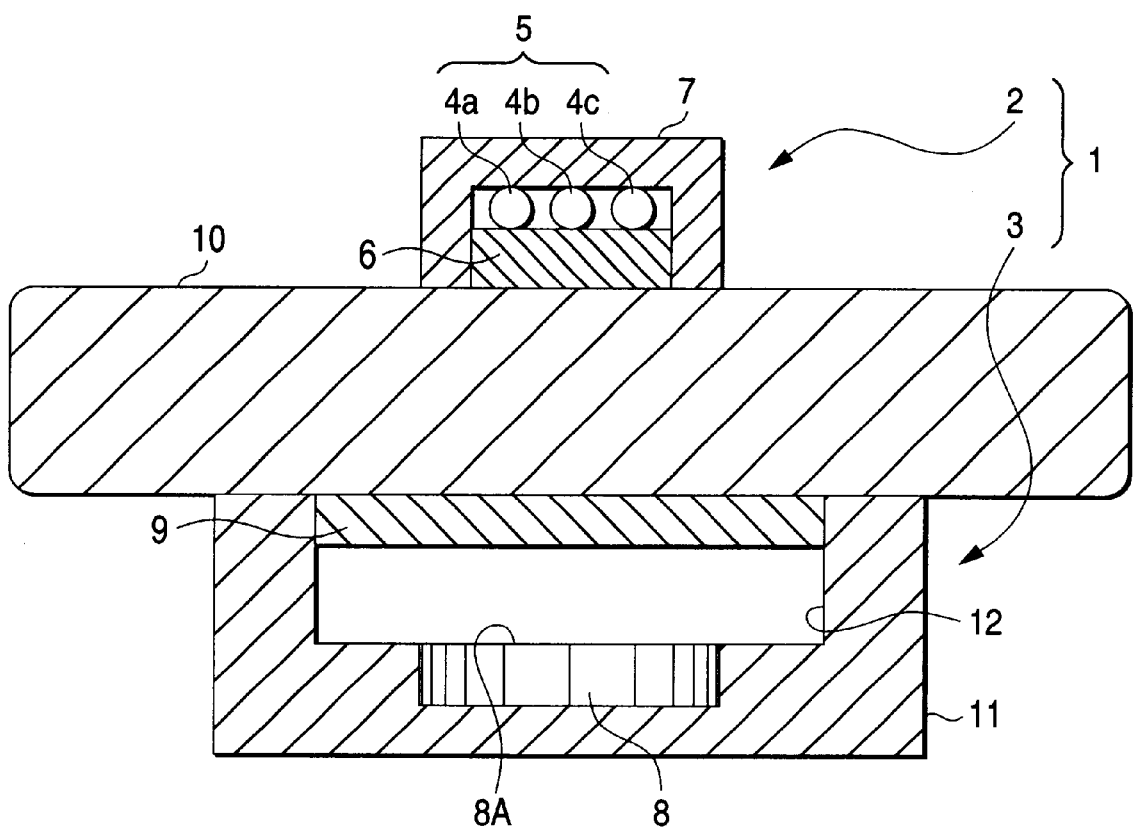
FIG. 1 is a cross sectional view showing a probe constructed according to the present invention.

To increase the number of the wavelengths for the measurement, the lights transmitted through the living tissue must be processed by using complicated computations. Therefore, theoretical formulas on the lights transmitted through the living tissue are needed, and those expressions must exactly describe actual phenomena. On the other hand, if the apparatus used for the measurement is complicated in construction and is hard to handle or too expensive, it is not practical. The apparatus must be as simple as possible in construction. For those reasons, an object of the present invention is to present the best construction of an optical system to operate the pulse photometry by using multiple wavelengths of lights. We will proceed with the object description in the following order: 1) the theory on the light transmitted through the living tissue; 2) the items required for an optical system to implement the exact coincidence of the predictions by the theoretical formulas with actual phenomena, and 3) a structure of the optical system to satisfy those required items.

1). Theoretical Formulas of the Pulse Photometry

Assuming that an intensity of incident light to a sample is Iin, and an intensity of light transmitted through the sample is Iout, an attenuation A may mathematically be defined as follows:

$$A = \log (Iin/Iout) \qquad (1)$$

If light scattering is absent, the attenuation A is expressed as;

$$A = ECD$$

Where E: extinction coefficient
C: concentration of a light absorbing material
D: thickness of the sample.
This relation is called the Lambert-Beer'slaw.

If a thickness of the sample is incremented by $\Delta D$, and the transmitted light is decremented by $\Delta Iout$, then, an increment $\Delta A$ of the attenuation is given by $$A + \Delta A = \log[Iin/(Iout - \Delta Iout)]$$

$$\Delta A = \log[Iout/(Iout - \Delta Iout)]$$

(1) If no light scattering is present, the above equations are $$A + \Delta A = EC(D + \Delta D) \cdot \Delta A = EC\Delta D$$

(2) If light scattering is present, $\Delta A$ will be given by $$\Delta A = \sqrt{E(E+F)} C \cdot \Delta D \qquad (2)$$

where F=scattering coefficient

Let us consider the measurement using two proper wavelengths $\lambda 1$ and $\lambda 2$. Assuming that transmitted lights of those wavelengths are I1 and I2, and decrements of the transmitted lights are $\Delta I1$ and $\Delta I2$, then we have $$\Delta A1 = \log [I1/(I1 - \Delta I1)] \equiv \Delta \log I1 \qquad (3)$$

$$\Delta A2 = \log [I2/(I2 - \Delta I2)] \equiv \Delta \log I2 \qquad (3)$$

Let us consider a case where two kinds of light-absorbing materials for a thickness increment are present, and their extinction coefficients are Ea and Eb, and their concentrations are Ca and Cb.

(1) No scattering is present, the attenuation increment $\Delta A$ is given by $$\Delta A1 = (EaCa + EbCb)\Delta D$$

Two kinds of the attenuation increments are obtained by using two wavelengths in measurement and the ratio $\phi$ of the two increments is obtained. As a result $\Delta A$ is removed and $\phi$ given by $$\phi = \Delta A1/\Delta A2 = (Ea1Ca + Eb1Cb)/(Ea2Ca + Eb2Cb) \quad (4)$$

where letters 1 and 2 attached indicate extinction coefficients of the respective wavelengths.

Accordingly, a ratio of concentrations Ca/Ab of the two materials can be obtained by measuring $$\phi = \Delta A1/\Delta A2 \quad (5)$$

(2) When the scattering is present:

It is assumed that the hemoglobin in the blood is a mixture of 02Hb and RHb, and the relative concentrations are So and Sr=1−So, and that the extinction coefficients are Eo and Er. Then, the attenuation increment $\Delta A$ is given by $$\Delta A = \sqrt{(EoSo + ErSr)(EoSo + ErSr + F)} Hb \cdot \Delta D \quad (6)$$

where Hb: hemoglobin concentration in the blood.

$$\phi = \Delta A1/\Delta A2 = \sqrt{(Eo1So + Er1Sr)(Eo1So + Er1Sr + F)}/\sqrt{(Eo2So + Er2Sr)(Eo2So + Er2Sr + F)} \quad (7)$$

Also in this case, a concentration ratio of the two materials is obtained by measuring the following relation $$\phi = \Delta A1/\Delta A2 \quad (8)$$

And based on this an oxygen saturation of the arterial blood is obtained by $$SaO2 = So \quad (9)$$

2. Optical System for the Pulse Photometry

The arterial blood is substantially uniformly distributed. Its substantial thickness periodically varies in synchronism with a pulsation of the heart. With the variation of the blood thickness, other tissues than the blood also vary in substantial thickness. As the result of those variations, the light transmitted through the tissue varies in a pulsating fashion.

Generally, the attenuation consists of two components.
(1) One of the components is a light scattering attenuation which is a light attenuation caused by only the scattering when no light absorption occurs.

This attenuation will be referred to as "non-absorbing attenuation". When parallel rays of light are scattered, the attenuation depends on the wavelength: the scattering attenuation is large when the wavelength of light is short and it is small when the wavelength is long. Rayleigh first mathematically proved this fact. Where the scattering of light rays is sufficiently large in degree, this wavelength-dependency disappears.

(2) The other component is an absorption attenuation. A light path is straight in a transparent sample. In the scattering sample, the light path is long since light is repetitively reflected and scattered. Accordingly, the absorption attenuation in the blood is higher than that in the transparent sample. If the following expression is calculated by detecting a pulsating variation that is synchronized with the heart pulsation, $$\Delta \log Iout = \Delta A, \quad (10)$$

then we have $$\Delta A = \Delta Aa + \Delta As$$

where $\Delta Aa$ is an absorbing attenuation and $\Delta As$ is non-absorbing attenuation. Most of the absorbing attenuation $\Delta Aa$ is caused by the arterial blood, and most of the non-absorbing attenuation $\Delta As$ is caused by other tissues than the blood. Generally, a variation of the thickness of the arterial blood and a variation of the thickness of other tissue than the arterial blood at that time are of reverse-phase. The same thing is true for the variations of the attenuation; when $\Delta Aa>0$, $\Delta As<0$ in mose cases. $\Delta As$ does not contain information on the light-absorbing material. Therefore, it is desirable that $\Delta Aa/\Delta As$ is large under the same condition.

From the above description, the items required for an optical system based on the pulse photometry are:
(1) The non-absorbing attenuation is not dependent on the wavelength.
(2) The affection of the absorbing attenuation by a thickness of the sample and the depth of the light-absorbing material of the sample is minimized.
(3) A ratio of absorbing attenuation/non-absorbing attenuation is large.

3. Structure and Characteristic of the Pulse-Photometry Basis Optical System

For discussion of a characteristic required for an optical system for the living tissue measurement, a model of it was established. For the living tissue, a material resembling in property the living tissue was used. Discussion to be given hereunder is based on the data gathered from the model and the material.

Figure 7A:
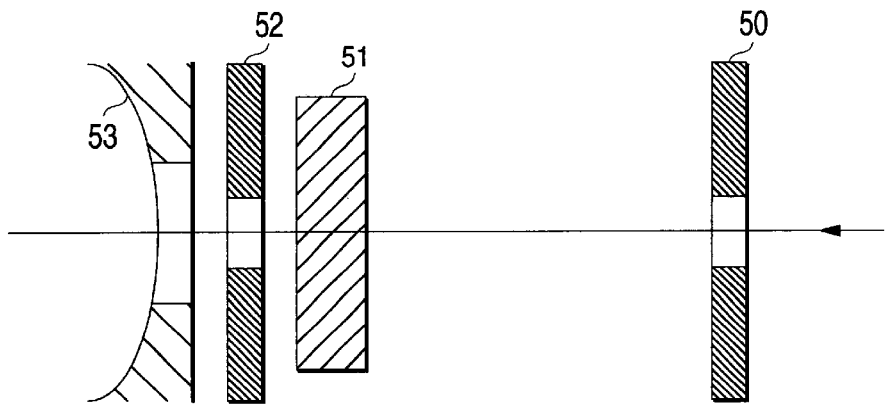
FIGS. 7 are diagrams showing apparatuses which simulate models of optical systems.

FIG. 7A is a diagram showing a model of an optical system in a normal pulse oximeter, which is constructed by using a spectro-photometer. A scheme of the model is common in many points to other optical systems, and hence somewhat detailed description will be given about it. The spectro-photometer is capable of emitting light of a single wavelength to a sample while sequentially changing its wavelength one to another. Light of the single wavelength enters the optical system, from the right hand side in the figure. An incident side mask 50 transforms the incident light into a light beam of 3 mm$\phi$. This is an simulation of a light source of the pulse oximeter the size of which is 3 mm$\phi$.

A sample 51 simulates the living tissue. Specifically, it was formed by laminating milky-white acryl plates of 1 mm thick one on the other by transparent adhesive. The scattering characteristic of the sample material resembles that of the living tissue. This fact was confirmed in another comparative experiment. Four samples 51 of 1 mm, 2 mm, 3 mm and 4 mm thick were manufactured. Those samples 51 are illustrated in front and side views in the column (a) in FIG. 15.

Figure 15:
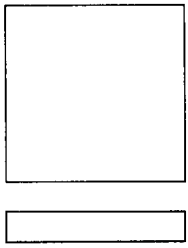
FIG. 15 is a diagram for explaining different samples used in the measurements by the FIGS. 7 and 8 apparatuses.

To simulate a light-absorbing material in the living tissue, other samples 51 were manufactured: a sheet of color film was applied to each sample 51 as shown in the column (b) in FIG. 15. In the figure, the color film is indicated by a bold line. In the sample 51 of 1 mm thick, the color film was bonded to the outer surface of the sample. In the sample of 2 mm thick, it was inserted between the two acryl plates of the sample.

In the sample of 3 mm thick, the color film was inserted into one of the joining interfaces of those acryl plates. Two samples of 4 mm thick were manufactured. In one sample, the color film was inserted into the joining interface located closer to one side of the sample structure. In the other sample, it was inserted into the center joining interface. The former sample whose color film is located not at the center joining interface was used as if the color film is located at two different positions in the sample structure by turning it. Accordingly, the sample of 1 mm thick was measured two times. (a) In the first measurement, the sample was located in a state that the color film is located on the incident side, and (b) in the second measurement, it was located in a state that the color film is located on the transmitted side. In the sample of 2 mm thick, it was measured one time in a state that the color film is located at the center of the sample. In the sample of 3 mm thick, it was measured two times. (C) In the first measurement, it was located in a state that the color film is located at the interface of the acryl plates, which is closer to the incident side. (d) In the second measurement, it was located at the interface of the acryl plates, which is closer to the transmitted side. In the sample of 4 mm thick, the sample was measured three times. (e) In the first measurement, the color film is located at the interface of the acryl plates, which is closer to the incident side. (f) In the second measurement, it was located at the to interface of the acryl plates, which is closer to the transmitted side. (g) In the third measurement, the color film was located at the interface of the acryl plates, which is located at the center of the sample. Those films were selected to be substantially equal in attenuation value. The milky-white acryl plates are notuniform in thickness. Accordingly, for the samples which are equal in nominal thickness, the acryl plates of equal thickness are selected and used.

Part of light transmitted through the sample 51 passes through a window of a transmit side mask 52. The transmit side mask 52 has a size of 4 mmφ. The size corresponds to an area of a light sensitive area of a light receiving device. An integral sphere 53 is used for measuring an intensity of light having passed through the transmit side mask 52. The integral sphere 53 is a ball of 60 mm in diameter whose inner wall is colored white. The integral sphere has a window formed therein. Light enters the integral sphere through the window, and is repeatedly scattered within the integral sphere to be uniformly distributed. In this state, a light intensity within the integral sphere is measured by a photo sensor. In the figure, a part of it is illustrated. In the figure, all the optical elements are separately depicted. Actually, however, only the incident side mask 50 is separated from the integral sphere 53 with a distance of about 20 mm, and other elements are in close contact with one another. The same thing is correspondingly applied to optical systems to subsequently be described.

The items tested by use of the simulation device are the wavelength dependency and magnitude of the non-absorbing attenuation and the magnitude of the absorbing attenuation. In the measurement of the non-absorbing attenuation, the samples 51 not IS using the color films were used. The thickness of the sample was gradually increased in the order of 1 mm, 2 mm, 3 mm and 4 mm. The wavelength characteristic on an increment of the attenuation when the number of the milky-white acryl plates of 1 mm thick is increased by one sheet, was measured.

Figure 9:
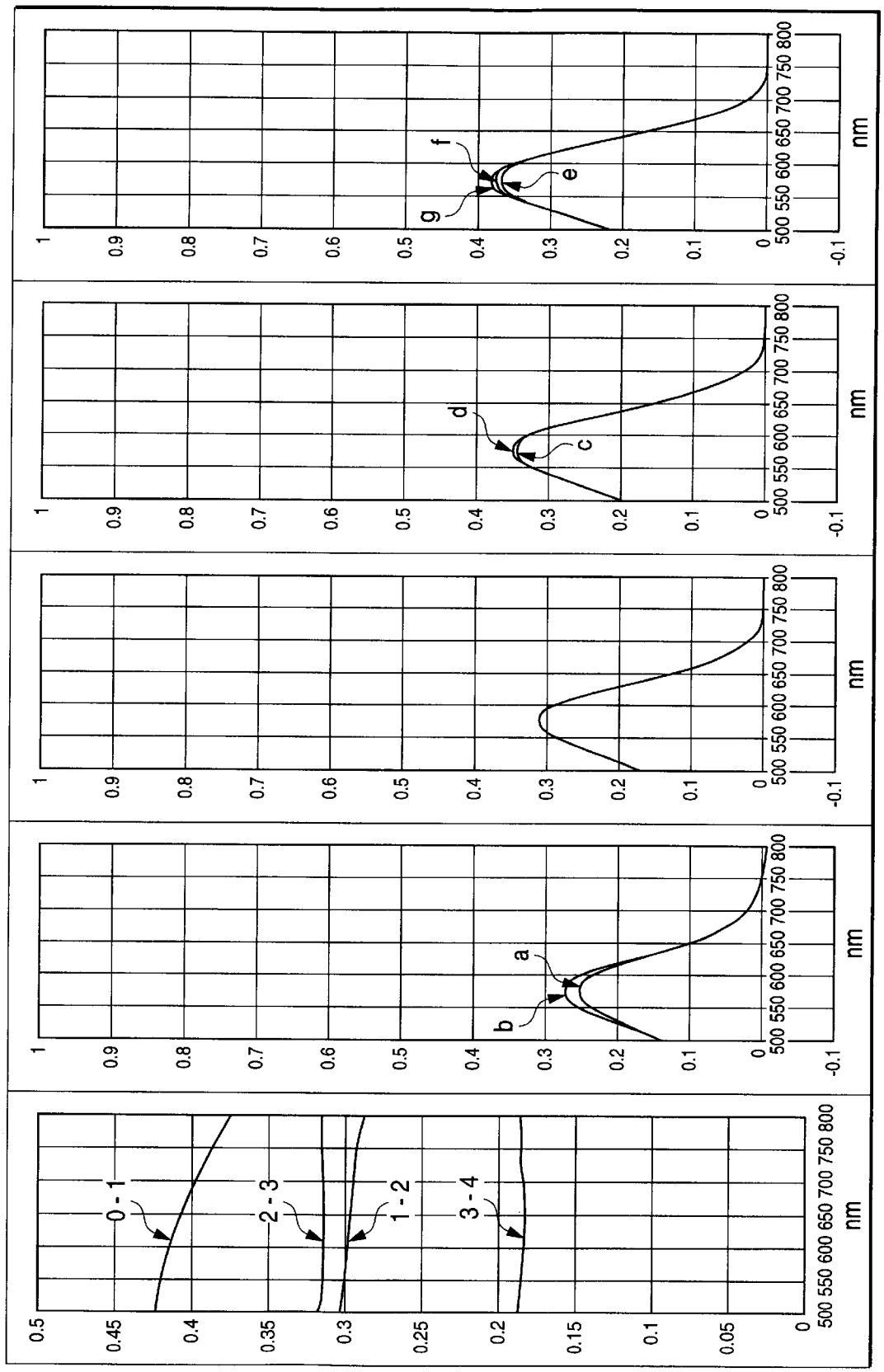
FIG. 9 graphically shows an attenuation characteristic of a sample, which is measured by use of the FIG. 7A apparatus.

In the measurement, the absorbing attenuation was obtained as a difference between the attenuation by the sample using the color film and the attenuation by the sample not using the same. FIG. 9 shows characteristics of the optical system on the wavelength-dependency of the non-absorbing attenuation and the absorbing attenuation. The leftmost graph in the figure shows a variation of the non-absorbing attenuation. In the figure, a curve 1–2 represents a variation of the attenuation caused by an additional acryl plate when a sheet of acryl plate is added to the sample 51 which is formed with one acryl plate. Curves 2–3 and 3–4 likewise represent a variation of the attenuation by an additional acryl plate when a sheet of acryl plate is added to the sample formed with two acryl plates, and a variation of the attenuation by an additional acryl plate when a sheet of acryl plate is added to the sample formed with three acryl plates. As seen from the graph, the non-absorbing attenuation depends on the wavelength, and is extremely large when a thickness of the sample is small in value. Those will cause an error in the pulse photometry.

A second graph and the subsequent ones as counted from the leftmost graph in the figure depict variations of absorbing attenuation when the sample 51 including the color film is increased in thickness in the order of 1 mm, 2 mm, 3 mm and 4 mm. (a) to (g) in the figure indicate the positions of the color film (The same thing is correspondingly applied to the subsequent figures.).

Those graphs show that the absorbing attenuation changes according to the thickness. This will also cause an error in the pulse photometry.

Figure 7B:
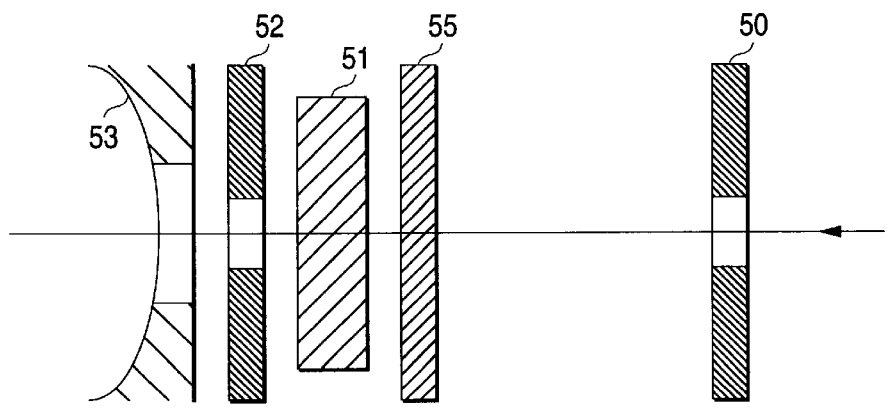
Figure 10:
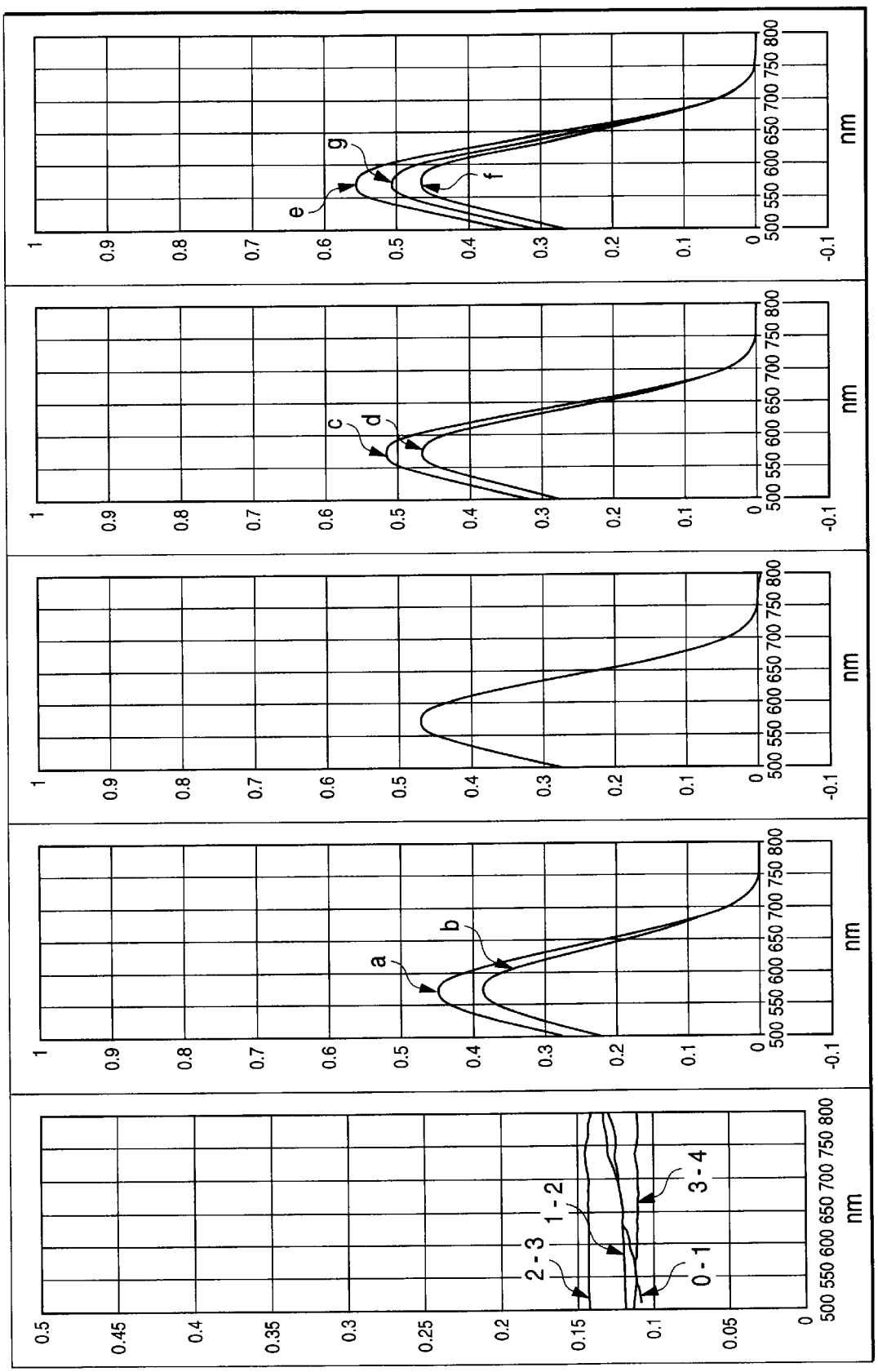
FIG. 10 graphically shows an attenuation characteristic of a sample, which is measured by use of the FIG. 7B apparatus.

FIG. 7B is a diagram showing a model of an optical system where a white acryl plate of 0.5 mmφ thick is used as a scattering plate 55 and located on the incident side of a sample. FIG. 10 graphically represents characteristics of the optical system on the wavelength-dependency of the non-absorbing attenuation and the absorbing attenuation. As seen, thewavelength characteristic of the non-absorbing attenuation and the thickness-dependency of the absorbing attenuation are both somewhat improved. However, the absorbing attenuation greatly varies depending on the position of the color film. This will cause an error in the pulse photometry.

Figure 7C:
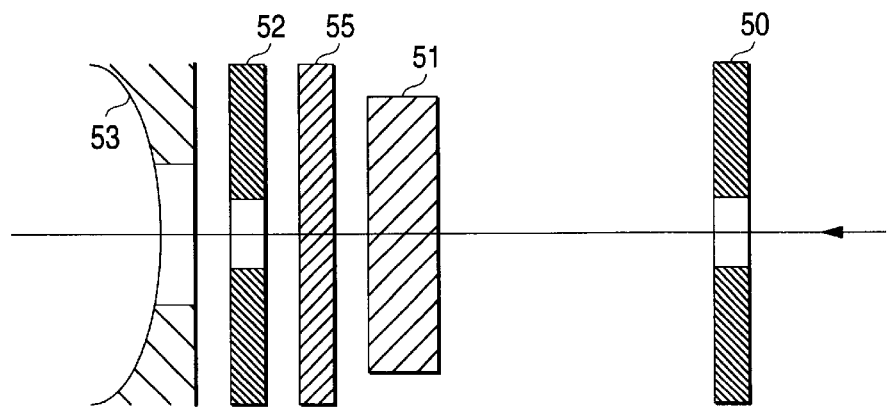
Figure 11:
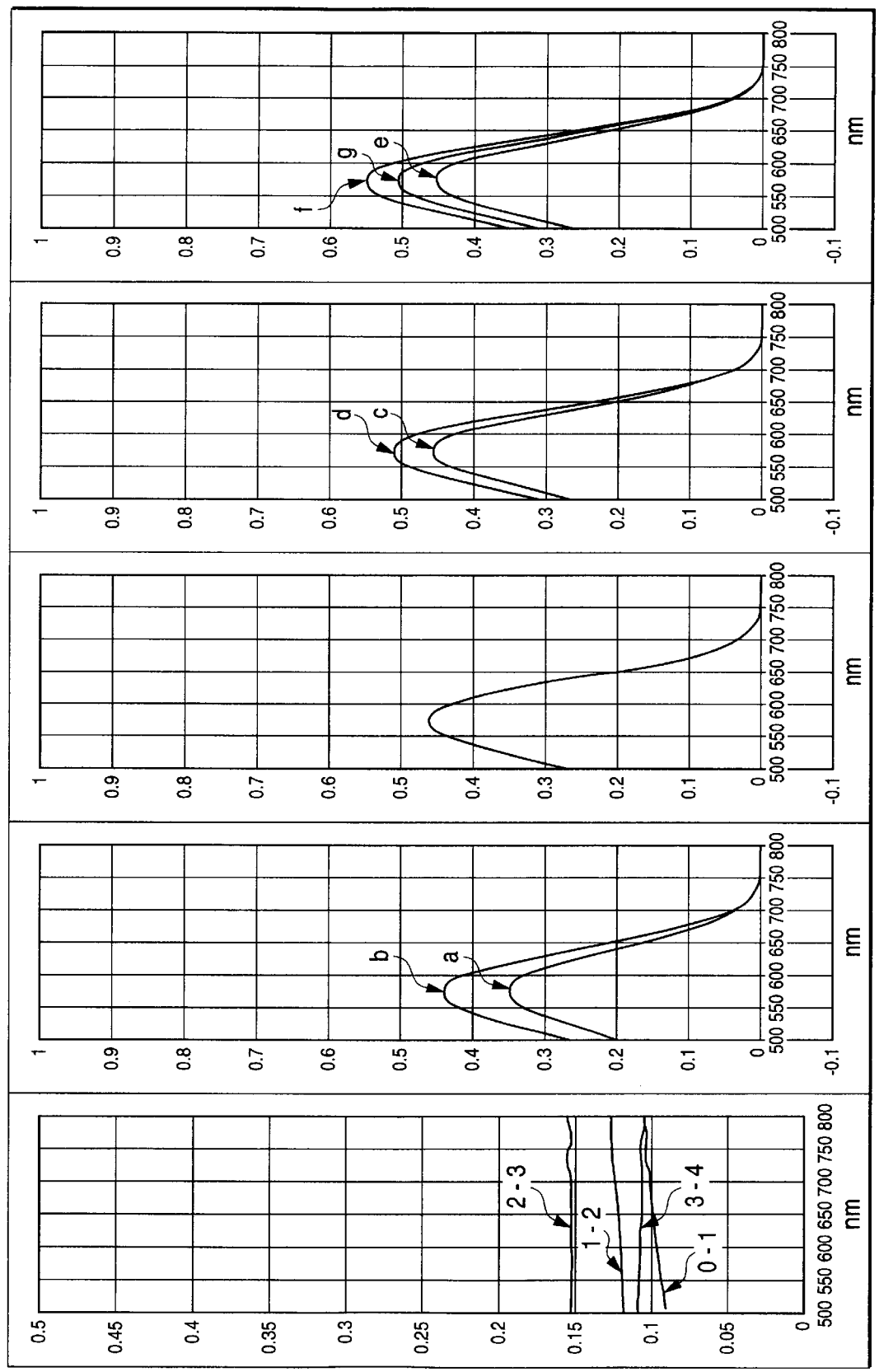
FIG. 11 graphically shows an attenuation characteristic of a sample, which is measured by use of the FIG. 7C apparatus.

FIG. 7C is a diagram showing a model of an optical system where a white acryl plate of 0.5 mm thick is used as a scattering plate 55 and located on the transmitted side of a sample. FIG. 11 graphically represents characteristics of the optical system on the wavelength-dependency of the non-absorbing attenuation and the absorbing attenuation. As seen, the characteristic curves on the measured items are a little different from those in the FIG. 10 case. However, the absorbing attenuation greatly varies depending on the position of the color film. The influence of the color film position upon the absorbing attenuation is reversed when comparing with that in the FIG. 10 case.

As seen from FIGS. 10 and 11, the fact that the absorbing attenuation is increased to be large is due to the fact that the light path is remarkably increased in a place near to the scattering plate 55. This would lead to the conclusion that the scattering plate 55 serves like a reflecting plate.

Figure 8A:
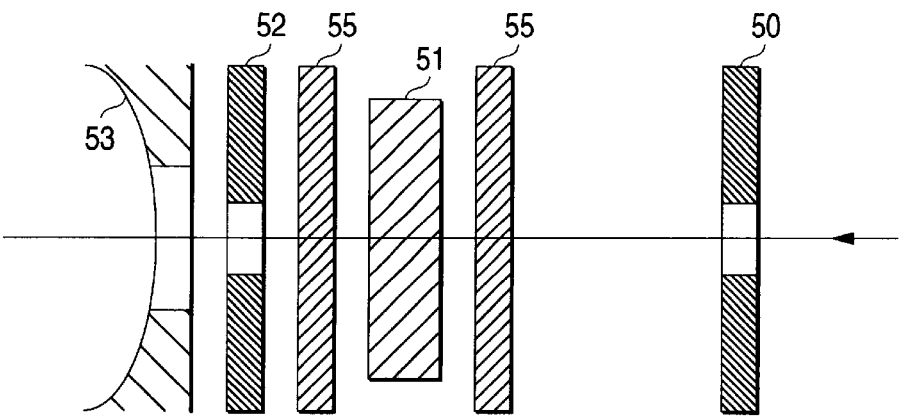
FIGS. 8 are diagrams showing apparatuses which simulate models of optical systems.
Figure 12:
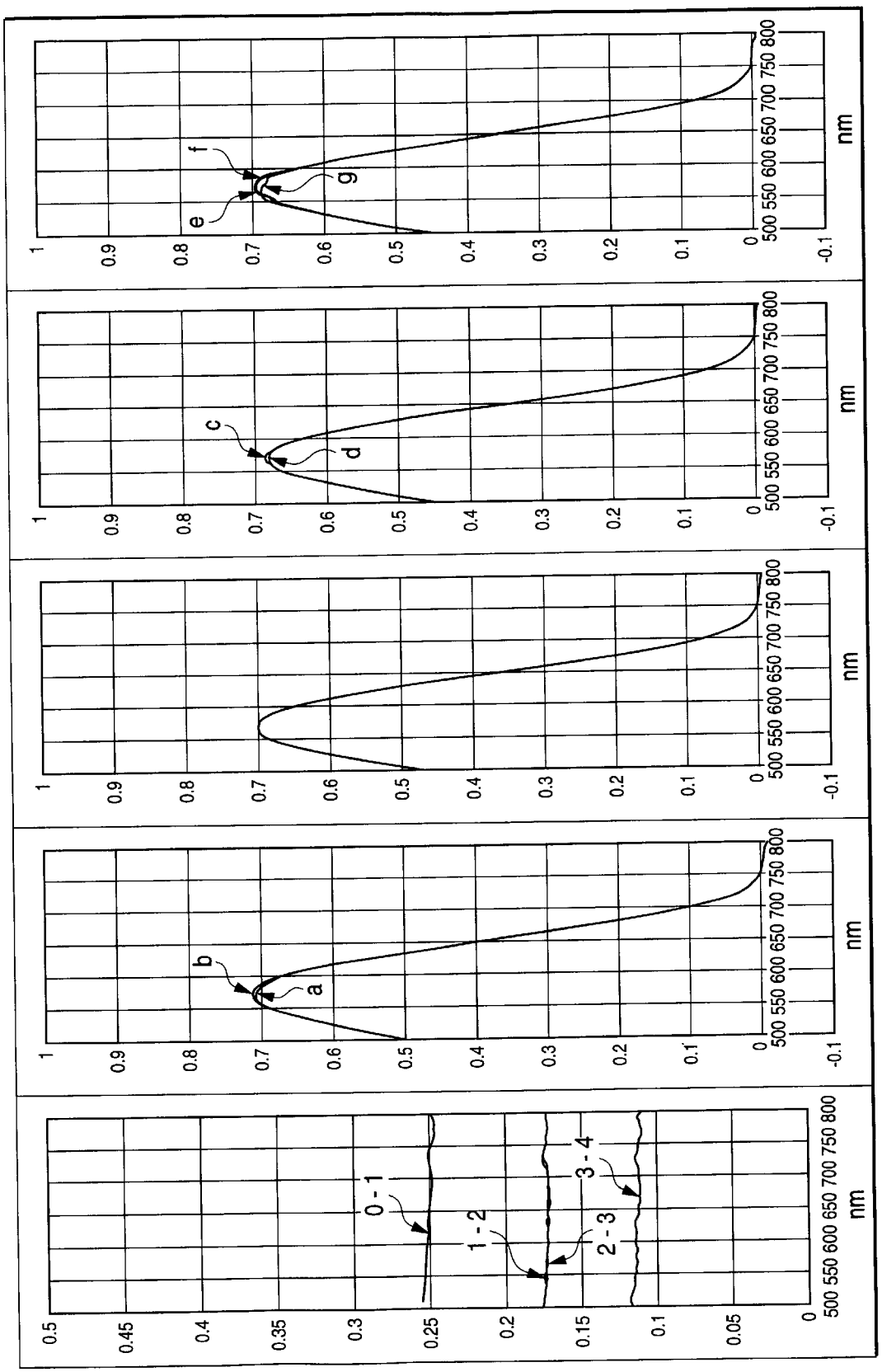
FIG. 12 graphically shows an attenuation characteristic of a sample, which is measured by use of the FIG. 8A apparatus.

In the optical system shown in FIG. 8A, white acryl plates of 0.5 mm thick as the scattering plates 55 are located on both sides of the sample 51, i.e., the incident side and the transmitted side. FIG. 12 graphically shows characteristics of the optical system on the wavelength-dependency of the non-absorbing attenuation and the absorbing attenuation. The curves representative of non-absorbing attenuation somewhat rise at the left end of the graph. This is caused by the light absorbing characteristic by transparent adhesive used. When this is taken into consideration, it will be seen that the wavelength dependency is successfully eliminated. Further, the graphs show that the influence of the plate thickness and the position upon the absorbing attenuation is removed, and the value of the absorbing attenuation is considerably increased. Those characteristics are suitable for the introduction of multiple wavelengths into the pulse photometry.

The merits produced when the proper scattering plate 55 are located at both the incident side and the transmitted side of the sample are elimination of the wavelength dependency of the non-absorbing attenuation and the thickness-dependency and position-dependency of the absorbing attenuation, and increase of the absorbing attenuation.

Figure 8B:
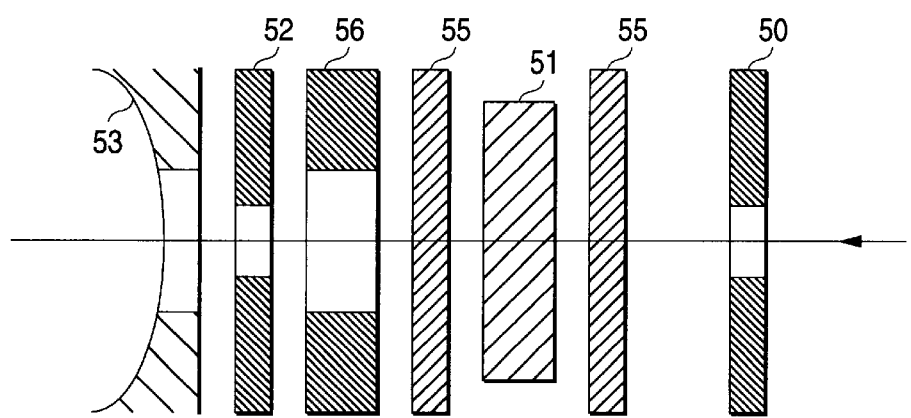
Figure 13:
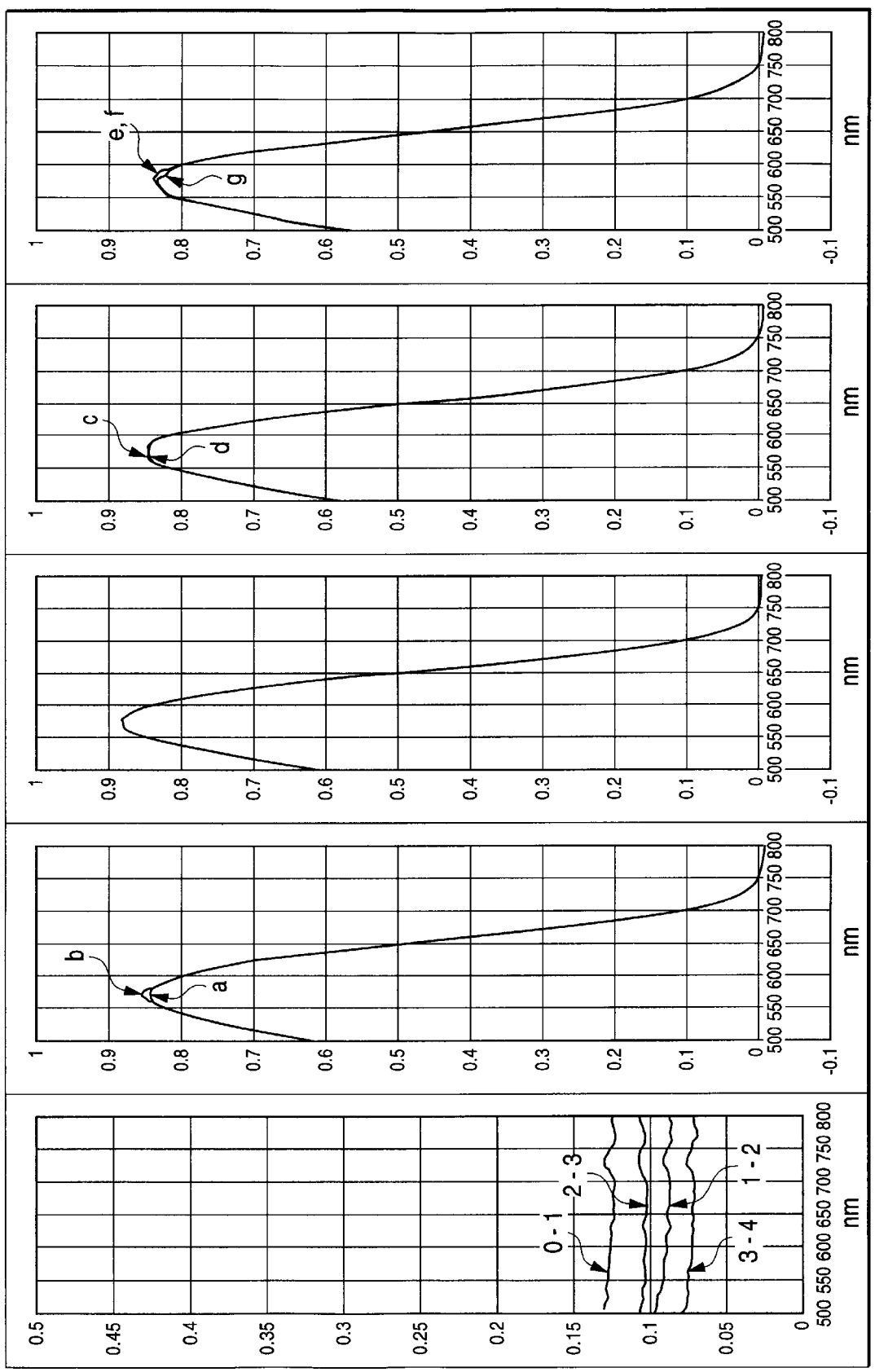
FIG. 13 graphically shows an attenuation characteristic of a sample, which is measured by use of the FIG. 7B apparatus.

FIG. 8B shows a model of an optical system arranged such that in the FIG. 8A optical system model, a light mixer 56 is located between the transmitted-side scattering plate 55 and the transmit side mask 52. The light mixer 56 is acylindrical cavity whose inner wall is colored white, and the transmit side mask 52 is also colored white. In this optical arrangement, light transmitted through the scattering plate 55 is mixed and passes is mixed and through the transmit side mask 52, and is received by the integral sphere. FIG. 13 graphically shows the characteristics of the optical system on the wavelength-dependency of the non-absorbing attenuation and the absorbing attenuation. As seen from the graphs, the non-absorbing attenuation is small in value. And the absorbing attenuation is increased in value. Those contribute to increase in the measuring accuracy. Use of such a light mixer is useful when an area of the light receiving element is smaller than an area of the light transmitted side on which it comes in contact with the living tissue.

In an actual probe, some restrictions are imposed thereon. Accordingly, the actual probe is inferior in performance to each of the FIGS. 8A and 8B cases. Specifically, the area of the former on which it comes in contact with the living tissue is limited, so that the area of the scattering plate is also limited. Further, the scattering plate attenuates light. Therefore, to efficiently use the limited intensity of the light from the LED, it is necessary to use the scattering plate as thin as possible.

Figure 8C:
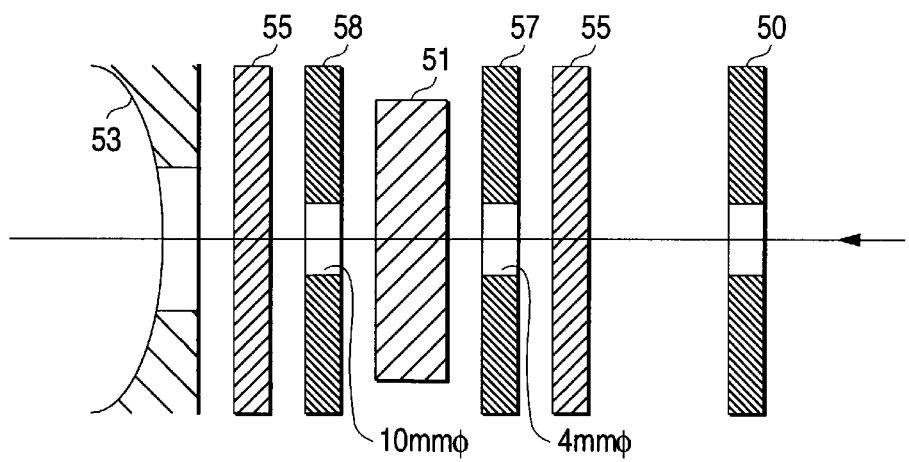
Figure 14:
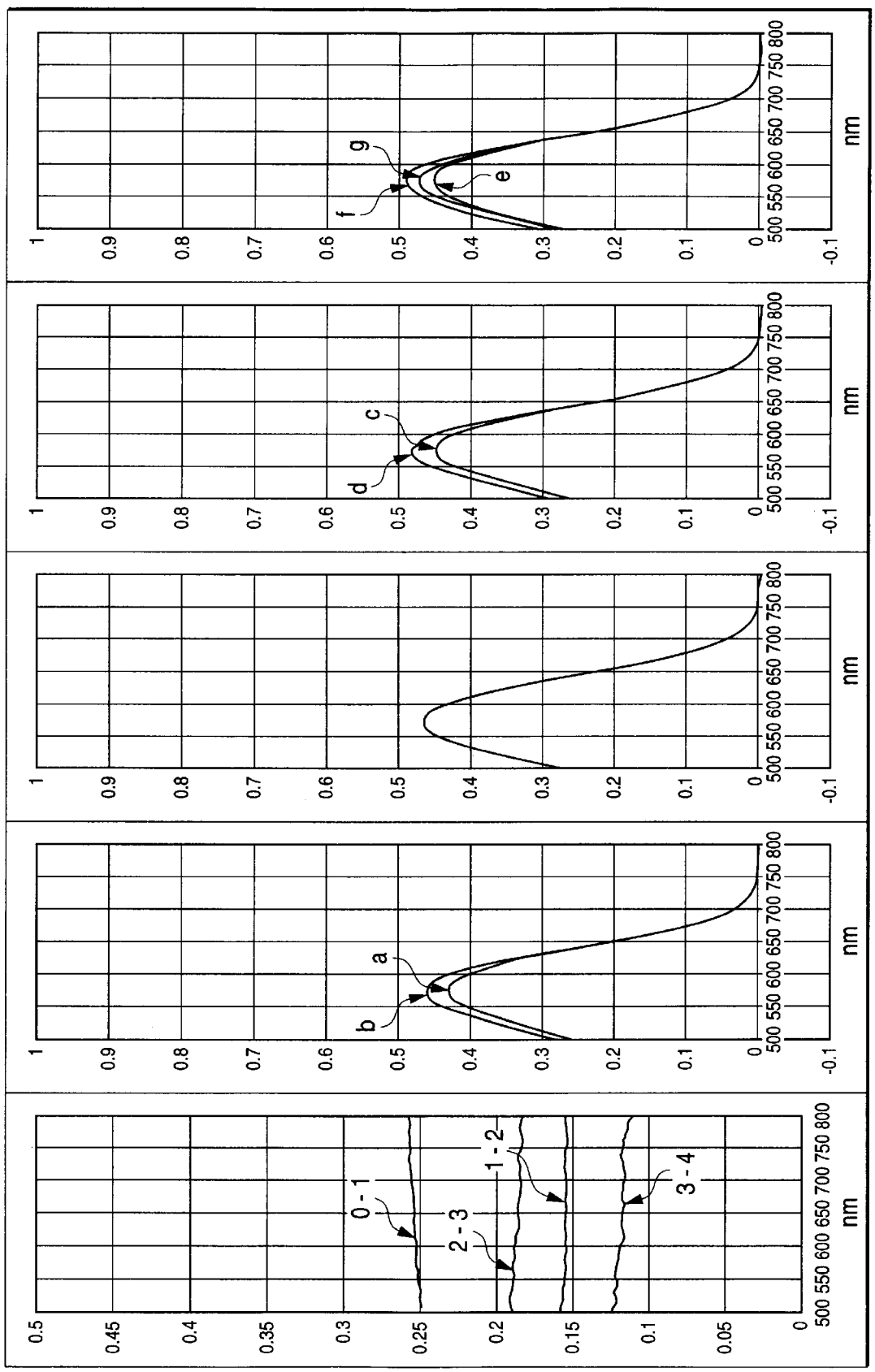
FIG. 14 graphically shows an attenuation characteristic of a sample, which is measured by use of the FIG. 8C apparatus.

An optical system shown in FIG. 8C is arranged while imaging an actual probe. In the optical system, the areas of the scattering plates 55 on which those may come in contact with the living tissue are 4 mmϕ (incident side) and 10 mmϕ (transmitted side). The scattering plates 55 were white acryl plates having a thickness of 0.25 mm. In the illustrated model, a mask 57 of 4 mmϕ is provided between the scattering plate 55 placed upstream of the sample 51 and the sample 51, and a mask 58 of 10 mmϕ thick is provided between the scattering plate 55 placed downstream of the sample 51and the sample 51. In the model, there is no need of using the mask placed downstream of the transmitted side scattering plate 55. Therefore, it is omitted. FIG. 14 graphically show characteristics of the optical system on the wavelength-dependency of the non-absorbing attenuation and the absorbing attenuation. Those characteristic curves resembles those in FIGS. 12 and 13, but are somewhat inferior to them as a whole.

A fluctuation of the measuring value is due to that the S/N ratio of the spectro-photometer is insufficient. When comparing with the characteristics of the FIG. 7A case as a model of the optical system of the conventional pulse oximeter, the wavelength dependency of the non-absorbing attenuation is almost eliminated and the measuring value is reduced to about ½. The thickness-dependency of the absorbing attenuation is considerably reduced. As for how the thickness-dependency of the absorbing attenuation affects ϕ, since ϕ=(ΔAa1+ΔAs1)/(ΔAa2+ΔAs2) as described above, the errors of the numerator and the denominator are substantially corrected by performing the division of them. For this reason, also in this case, those characteristics, which are much better,can be expected.

Preferred Embodiments
First Embodiment

A pulse oximeter using three wavelengths will be described as a first embodiment of the present invention. A conventional pulse oximeter is of the 2-wavelength type. The pulse oximeter of the 3-wavelength type is improved over the 2-wavelength pulse oximeter in the performance.

The principle of the 3-wavelength pulse oximeter will first be described. One of the major causes of an error in the conventional pulse oximeter is a pulsation other than a pulsation of the arterial blood. This is the non-absorbing attenuation ΔAs and varies due to a mounting state of the probe and others. This is also a large component of the artifact caused by a body movement. To lessen the influence by ΔAs, light emitted from a light source is scattered by a scattering portion and then irradiated onto living tissue as an object under measurement, and light received from the living tissue is passed through the scattering portion and then applied to a light sensitive surface of a photo-electric transducing portion.

By using this optical system, lights transmitted through living tissue are measured with proper three wavelengths λ1, λ2 and λ3, and ΔA1, ΔA2 and ΔA3 are obtained based on the measurement results. From those ΔA1, ΔA2 and ΔA3, we have $$\phi 12 = \Delta A1/\Delta A2 \tag{11}$$

$$\phi 32 = \Delta A3/\Delta A2 \tag{11}$$

Those are substituted into the following expressions.

$$\phi 12 = \Delta A1/\Delta A2 = (\Delta Aa1 + \Delta As1)/(\Delta Aa2 + \Delta As2) \tag{12}$$

$$\phi 32 = \Delta A3/\Delta A2 = (\Delta Aa3 + \Delta As)/(\Delta Aa2 + \Delta As2) \tag{12'}$$

This simultaneous equations will be described in detail. If ΔAa is expressed by the expression (6), ΔAa1, ΔAa2 and ΔAa3 are given by the following expressions:

$$\Delta Aa1 = \sqrt{(Eo1So + Er1Sr)(Eo1So + Er1Sr + F)} Hb\Delta D \tag{13}$$

$$\Delta Aa2 = \sqrt{(Eo2So + Er2Sr)(Eo2So + Er2Sr + F)} Hb\Delta D \tag{13'}$$

$$\Delta Aa3 = \sqrt{(Eo3So + Er3Sr)(Eo3So + Er3Sr + F)} Hb\Delta D \tag{13''}$$

Accordingly, ϕ12 is given by $$\phi 12 = \Delta A1/\Delta A2 = [\sqrt{(Eo}$$

$$1So + Er1Sr)(Eo1So + Er1Sr + F)Hb\Delta D +$$

$$\Delta As1]/[\sqrt{(Eo2So + Er2Sr)}$$

$$(Eo2So + Er2Sr + F)Hb\Delta D + \Delta As2]$$

$$= (\sqrt{(Eo1So + Er1Sr)}$$

$$(Eo1So + Er1Sr + F) + \Delta As1/Hb$$

$$\Delta D]/[\sqrt{(Eo2So + Er}$$

$$2sr)(Eo2So + Er2Sr + F) +$$

$$\Delta As2/Hb\Delta D] \tag{14}$$

ϕ32 is likewise given by $$\phi 32 = \Delta A3/\Delta A2 = [\sqrt{}$$

$$(Eo3So + Er3Sr)(Eo3So + Er$$

$$3Sr + F) + \Delta As3/Hb\Delta D]/[\sqrt{}$$

$$\sqrt{(Eo2So + Er2Sr)(Eo}$$

$$2So + Er2Sr + F) + \Delta As2/Hb\Delta D] \tag{15}$$

In the optical system, ΔAs1, ΔAs2 and ΔAs3 are ideally equal in value. Accordingly, the ratios ΔAs1/HbΔD, ΔAs1/HbΔD, and ΔAS1/HbΔD are also equal in value.

Let the value be E. Relation sr=1−So holds. Therefore, the expressions (14) and (15) are simultaneous equations having two unknown values So and Ex. $\phi12$ and $\phi32$ may be obtained from $\Delta A1$, $\Delta A2$ and $\Delta A3$ gathered through the measurement. Thence, the simultaneous equations can be solved. Here, So=SaO2 (oxygen saturation in the artery blood). The thus obtained SaO2 is not affected by $\Delta As$. Accordingly, it is a highly accurate value.

Next, an apparatus constructed on the basis of the principle mentioned above will be described. A cross sectional view of a probe of the apparatus is shown in FIG. 1.

As shown, a probe 1 is generally made up of a light irradiating device 2 for generating scattering light and a light receiving device 3. The light irradiating device 2 includes a light source consisting of three LEDs 4a, 4b and 4c, and a scattering plate for scattering light received from the light source 5. Those three LEDs 4a, 4b and 4c of the light source 5 are mounted on the inner wall of a housing 7, which is confronted with an opening of the housing. The scattering plate 6 is fit into the opening. The three LEDs 4a, 4b and 4c generate lights having different wavelengths $\lambda1$, $\lambda2$ and $\lambda3$, respectively. Those wavelengths are. $\lambda1=800$ nm, $\lambda2=900$ nm and $\lambda3=650$ nm. If necessary, the wavelengths may take other values. The scattering plate 6 is preferably a white acryl plate. The scattering plate 6 forms a first light scattering portion.

As shown in FIG. 1, the light irradiating device 2 and the light receiving device 3 are oppositely disposed sandwiching living tissue (e.g., finger or earlobe) 10 therebetween. The probe 1 is provided with holding means (not shown) which tightly holds the living tissue 10 with the light irradiating device 2 and the light receiving device 3.

The light receiving device 3 includes one photo diode (photo-electric transducing means) 8, a light scattering plate 9 located in front of a light sensitive surface 8A of the photo diode 8, and a housing 11 for holding them. The housing 11 includes a cylindrical cavity opened at one end, and the photo diode 8 is set in a recess formed in the bottom of the housing 11. The light scattering plate 9 as a plate like member is set in the opening of the housing 11, and the outer surface of the light scattering plate 9 is flush with the end face of the housing 11. An area of the light sensitive surface 8A of the photo diode 8 is smaller than that of the light scattering plate 9. Scattering light passed through the light scattering plate 9 is mixed when it passes through the cavity of the housing 11. Light incident on the light sensitive surface 8A is formed by substantially uniformly sampling the light transmitted through the light scattering plate 9. An amount of receiving light may be increased by coloring the inner wall of the housing 11 white. In this instance, the light scattering plate 9 is a second light scattering portion, and the inner wall of the housing 11, which forms the cavity portion, forms a light mixing portion.

Figure 2:
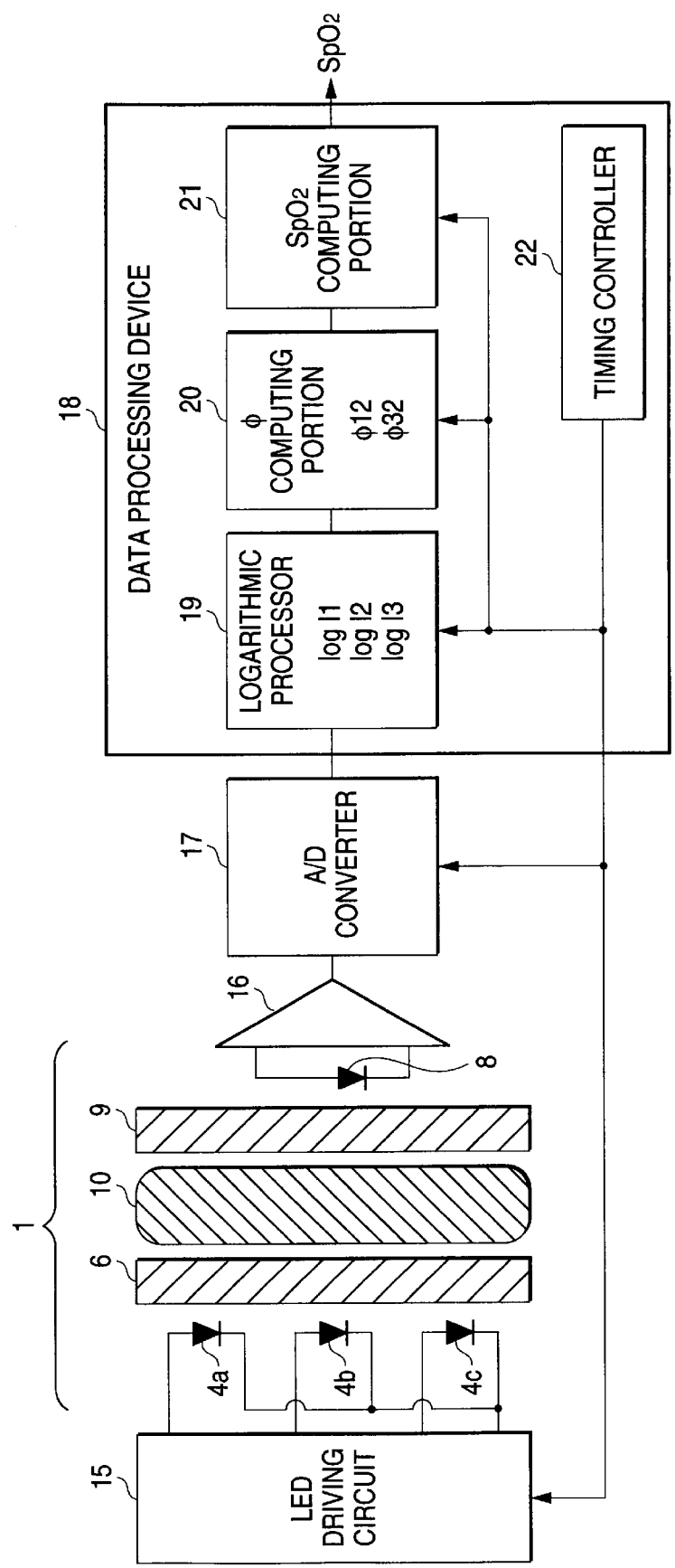
FIG. 2 is a block diagram showing an arrangement of a pulse oximeter using the FIG. 1 probe.

An overall arrangement of the apparatus is shown in FIG. 2. The LEDs 4a, 4b and 4c of the probe 1 are one by one lighted by a LED driving circuit 15. An electrical signal produced from the photo diode 8 of the probe 1 is amplified by an amplifier 16, and input to an A/D converter 17 where it is digitized, and is processed by a data processor 18.

The data processor 18 includes a logarithmic processor 19, a $\phi$ computing portion 20, an SpO2 computing portion 21, and a timing controller 22. The logarithmic processor 19 receives a signal from the A/D converter 17 and converts it into a logarithmic signal. A signal output from the A/D converter 17 contains information of intensities I1, I2 and I3 of lights transmitted through the living tissue 10. The logarithmic processor 19 logarithmically converts the signal into signals indicative of logI1, logI2 and logI3.

The $\phi$ computing portion 20 processes those signals into $\phi12$ and $\phi32$ in a computing manner. That is, it computes the following expressions.

$\phi12=\Delta A1/\Delta A2=\Delta \log I1/\Delta \log I2$ $\phi32=\Delta A3/\Delta A2=\Delta \log I3/\Delta \log I2$ The SpO2 computing portion 21 computes the following simultaneous equations of $\phi12$ and $\phi32$ having two unknown values So and Ex (see the expressions (14) and (15))

$\phi12=\Delta A1/\Delta A2=[\sqrt{(Eo1So+Er1Sr)(Eo1So+Er1Sr+F)+Ex}]/[\sqrt{(Eo2So+Er2Sr)(Eo2So+Er2Sr+F)+Ex)}$ $\phi32=\Delta A3/\Delta A2=[\sqrt{(Eo3So+Er3Sr)(Eo3So+Er3Sr+F)+Ex}]/[\sqrt{(Eo2So+Er2Sr)(Eo2So+Er2Sr+F)+Ex]}$ By the computation, So, or oxygen saturation SpO2, is obtained.

The timing controller 22 is a circuit for controlling operation timings of the related circuit portions.

An operation of the apparatus thus arranged will now be described hereunder. An operator sets the probe 1 to the living tissue 10 of a patient, such as a finger tip or an earlobe. In this case, the living tissue 10 is tightly sandwiched between the scattering plate 6 of the light irradiating device 2 and the light scattering plate 9 of the light receiving device 3.

Then, the operator turns on the apparatus, and in turn the LEDs 4a, 4b and 4c are selectively lighted at the timings controlled by the timing controller 22. Lights emitted from the LEDs 4a, 4b and 4c reaches the light mixing portion 12 by way of the scattering plate 6, the living tissue 10 and the light scattering plate 9. The lights are mixed in the light mixing portion and reaches the light sensitive surface of the photo diode 8, and are converted into electrical signals by the photo diode 8. The signals are amplified by the amplifier 16, digitized by the A/D converter 17, and reach the logarithmic processor 19. The logarithmic processor 19 logarithmically converts those signals into signals representative of logI1, log I2 and logI3, and outputs the converted ones to the $\phi$ computing portion 20. The $\phi$ computing portion 20 performs the above-mentioned computing operation by using those signals to produce $\phi12$ and $\phi32$, and outputs them to the SpO2 computing portion 21. The SpO2 computing portion 21 performs the computing operation to produce an oxygen saturation SpO2. The thus obtained oxygen saturation SpO2 is displayed by display means (not shown), and recorded by a recorder (not shown).

An apparatus for performing the measurement on a dye dilution curve, which is a second embodiment of the present invention, will be described. The apparatus is based on the following simultaneous equations, and uses four wavelengths of lights.

$\phi12=\Delta A1/\Delta A2=[\sqrt{(Eh1+Ed1Cd/Hb)(Eh1+Ed1Cd/Hb+F)+Ex}]/[\sqrt{(Eh2+Ed2Cd/Hb)(Eh2+Ed2Cd/Hb+F)+Ex]}$ (17)

$\phi32=\Delta A3/\Delta A2=[\sqrt{(Eh3+Ed3Cd/Hb)(Eh3+Ed3Cd/Hb+F)+Ex}]/[\sqrt{(Eh2+Ed2Cd/Hb)(Eh2+Ed2Cd/Hb+F)+Ex]}$ (17')

$\phi42=\Delta A4/\Delta A2=[\sqrt{(Eh4+Ed4Cd/Hb)(Eh4+Ed4Cd/Hb+F)+Ex}]/[\sqrt{(Eh2+Ed2Cd/Hb)(Eh2+Ed2Cd/Hb+F)+Ex]}$ (17")

Here, Ehi=EoiSo+Eri(1−So)(i=1, 2, 3, 4), Edi (i=1, 2, 3, 4) is an extinction coefficient of dye to be injected into a blood vessel, Cd is a concentration of dye in the blood, and Hb is a hemoglobin concentration. The simultaneous equations have three unknown values So, Cd, Ex. A dye dilution curve is obtained by solving the equations and successively measuring the dye concentration Cd in the blood.

Figure 3:
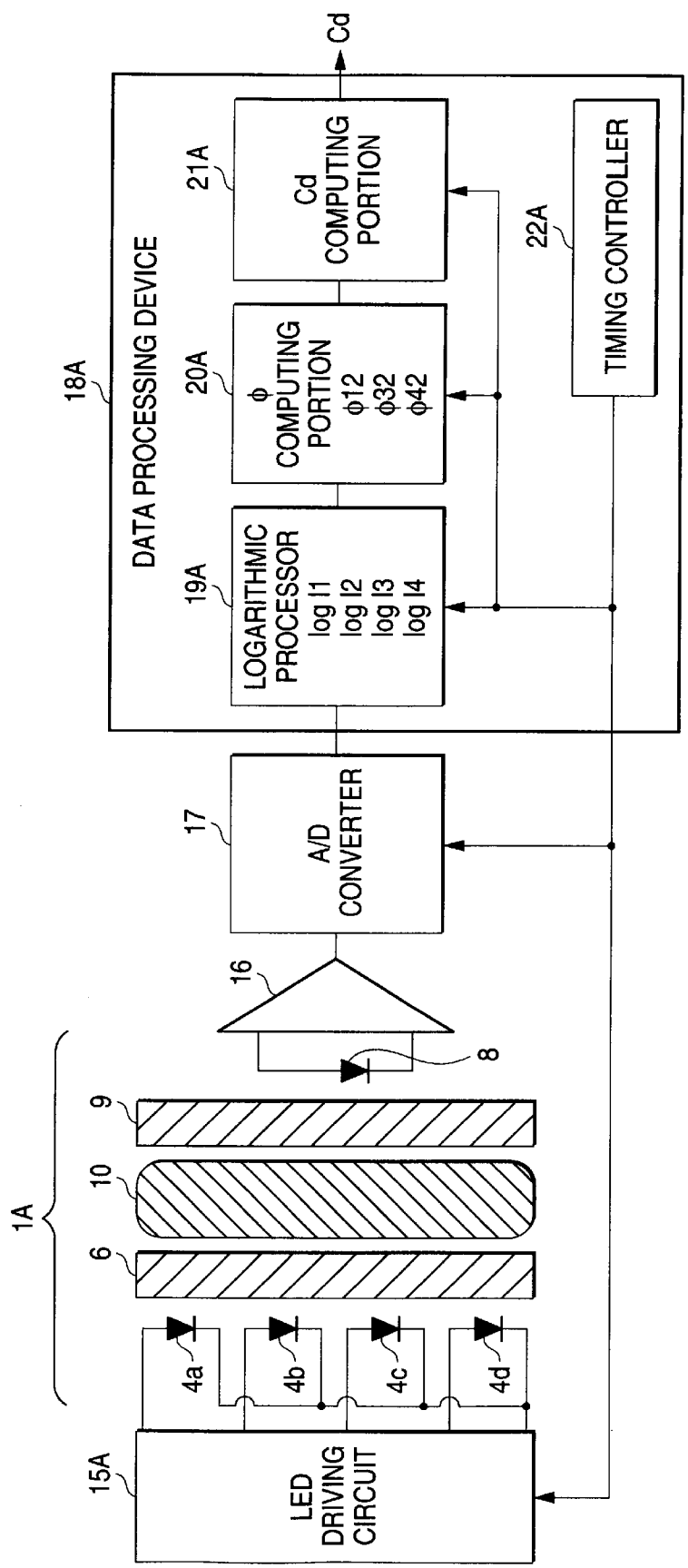
FIG. 3 is a block diagram showing a dye-dilution-curve measuring apparatus using the FIG. 1 probe.

An arrangement of an apparatus based on this principle is shown in FIG. 3. The arrangement of the apparatus is substantially the same as that of the FIG. 2 apparatus, although the number of wavelengths is increased by one. A specific construction of a probe 1A shown in FIG. 3 is substantially the same as that of the FIG. 1 apparatus except that the number of LEDs is increased by one (the additional LED is designated by reference numeral 4d in FIG. 3). Therefore, the detailed description of its construction is omitted here.

The apparatus will be described with reference to FIG. 3. A timing controller 22a of a data processor 18A controls operation timings of the related portions. A LED driving circuit 15A selectively lights LEDs 4a, 4b, 4c and 4d at the operation timings controlled by the timing controller 22A. Lights emitted from LEDs 4a, 4b, 4c and 4d reach the light sensitive surface of the photo diode 8 by way of the scattering plate 6, the living tissue 10, the light scattering plate 9, and a light mixing portion (not shown). Those lights are converted into electric signals by the photo diode 8. The signals are amplified by the amplifier 16 and digitized by the A/D converter 17, and input to a data processor 18A. In the data processor 18A, a logarithmic processor 19A logarithmically converts those signals into signals of logI1, logI2, logI3 and LogI4. Those signals are then input to the i computing portion 20A. The $\phi$ computing portion 20A processes those signals to produce $\Delta A1 = \Delta \log I1$, $\Delta A2 = \Delta \log I2$, $\Delta A3 = \Delta \log I3$, $\Delta A4 = \Delta \log I4$, further computes $\phi 12 = \Delta A1/\Delta A2$, $\phi 32 = \Delta A3/\Delta A2$, $\phi 42 = \Delta A4/\Delta A2$, and outputs the computed ones, $\phi 12$, $\phi 32$ and $\phi 42$ to a Cd computing portion 21A. The Cd computing portion 21A computes the simultaneous equations to produce a concentration of dye injected into the blood vessel. The dye concentration Cd obtained is displayed by display means (not shown) and recorded by a recorder (not shown).

The apparatus thus arranged may be applied to the measurement of another material, such as in-blood light absorbing material CoHb.

In each of the probes used in the above-mentioned embodiments, the light mixing portion is provided in the light receiving device. To reduce the probe in size or in thickness, a construction shown in FIG. 4 may be employed omitting the light mixing portion. To be specific, in the construction, the inner surface of a scattering plate 31 of a light receiving device 30 is brought into close contact with the light sensitive surface of the photo diode 8. In this case, an end face 32A of a housing 32, which is in contact with the scattering plate 31, is colored white. The remaining construction of the probe is the same as that in the FIG. 1 probe. Therefore, reference numerals are used for designating like or equivalent portions in FIG. 1. In the probe thus constructed, light from the scattering plate 31 is reflected by the end face 32A of the housing 32, so that an intensity of the transmitted light is increased. In this instance, the scattering plate 31 and the end face 32A form the second light scattering portion.

In each of the probes used in the above-mentioned embodiments, the second light scattering portion uses a scattering plate. To increase an intensity of the transmitted light in the probe, a transparent plate may be used in lieu of the scattering plate in FIG. 1 or 4. In this case, the reflecting surface of the light mixing potion in FIG. 1 or the housing surface in FIG. 4 serves as the second light scatting portion.

Figure 4:
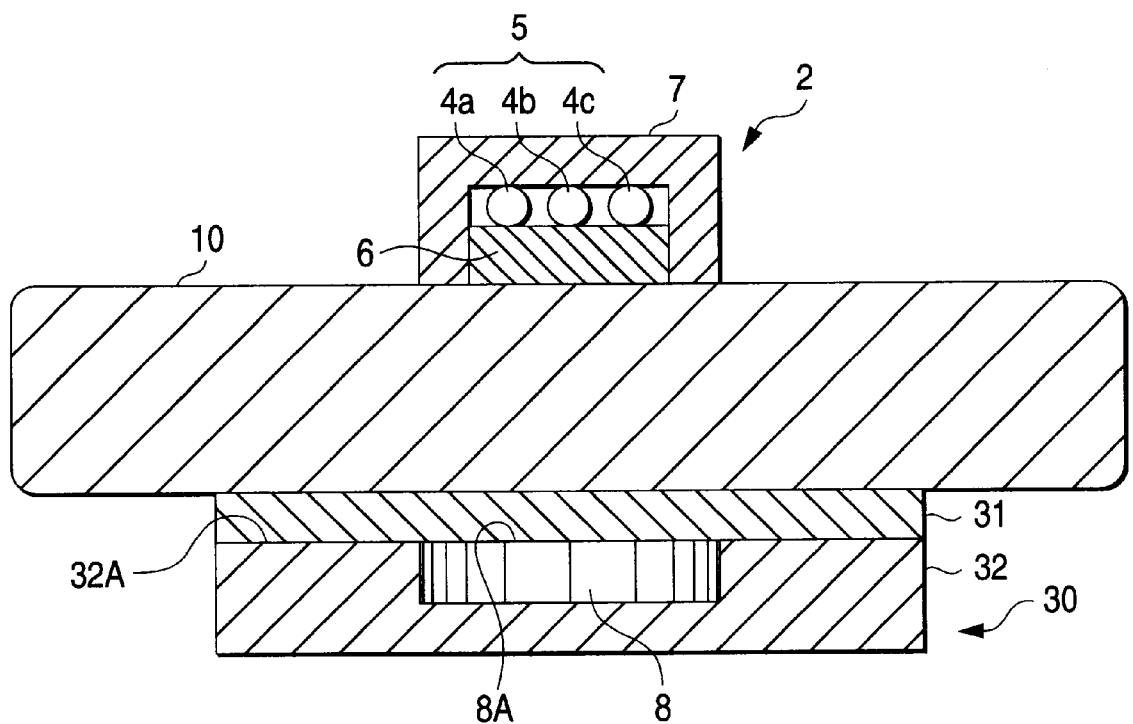
FIG. 4 is a cross sectional view showing another probe according to the present invention.
Figure 5:
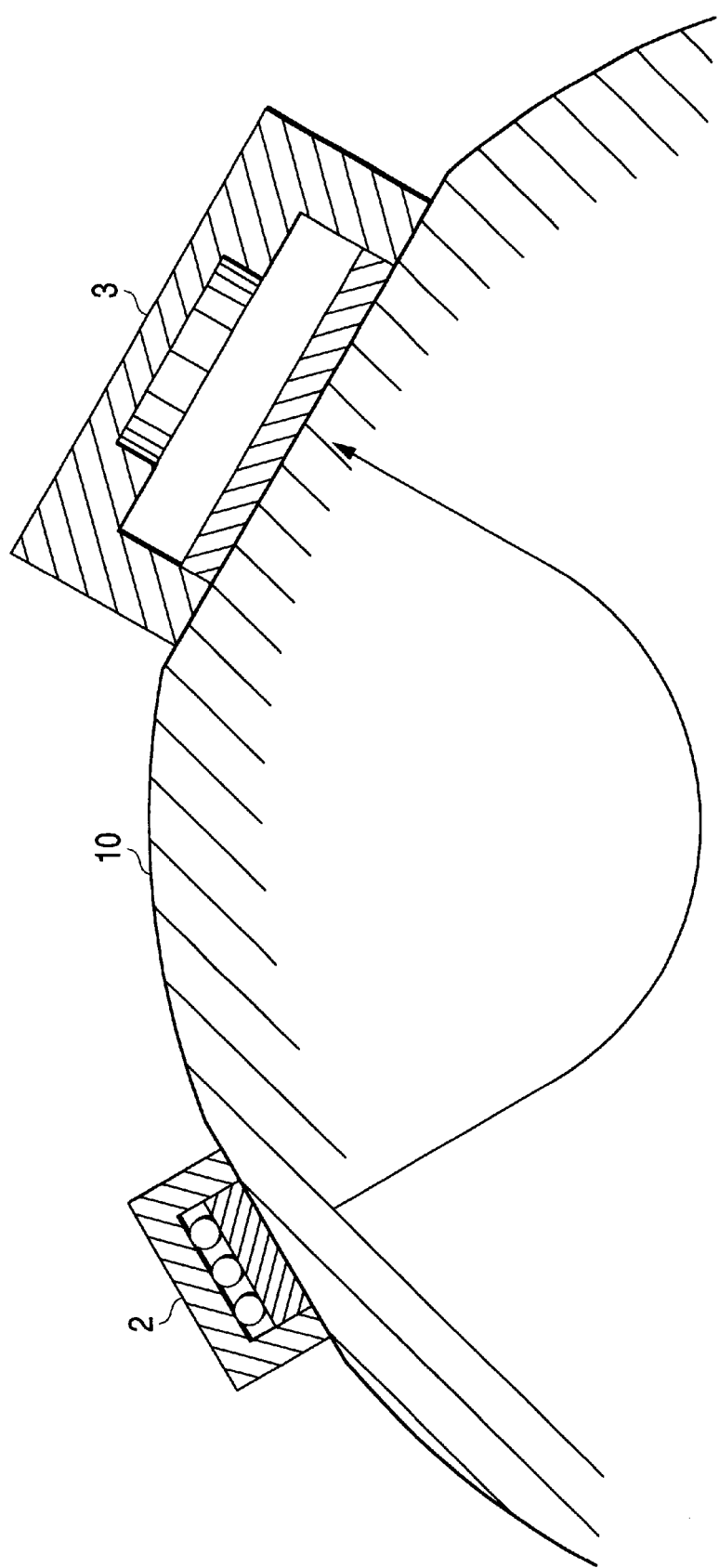
FIG. 5 is a cross sectional view showing yet another probe according to the present invention, the reflection type probe with the same construction of the probe shown in FIG. 1.
Figure 6:
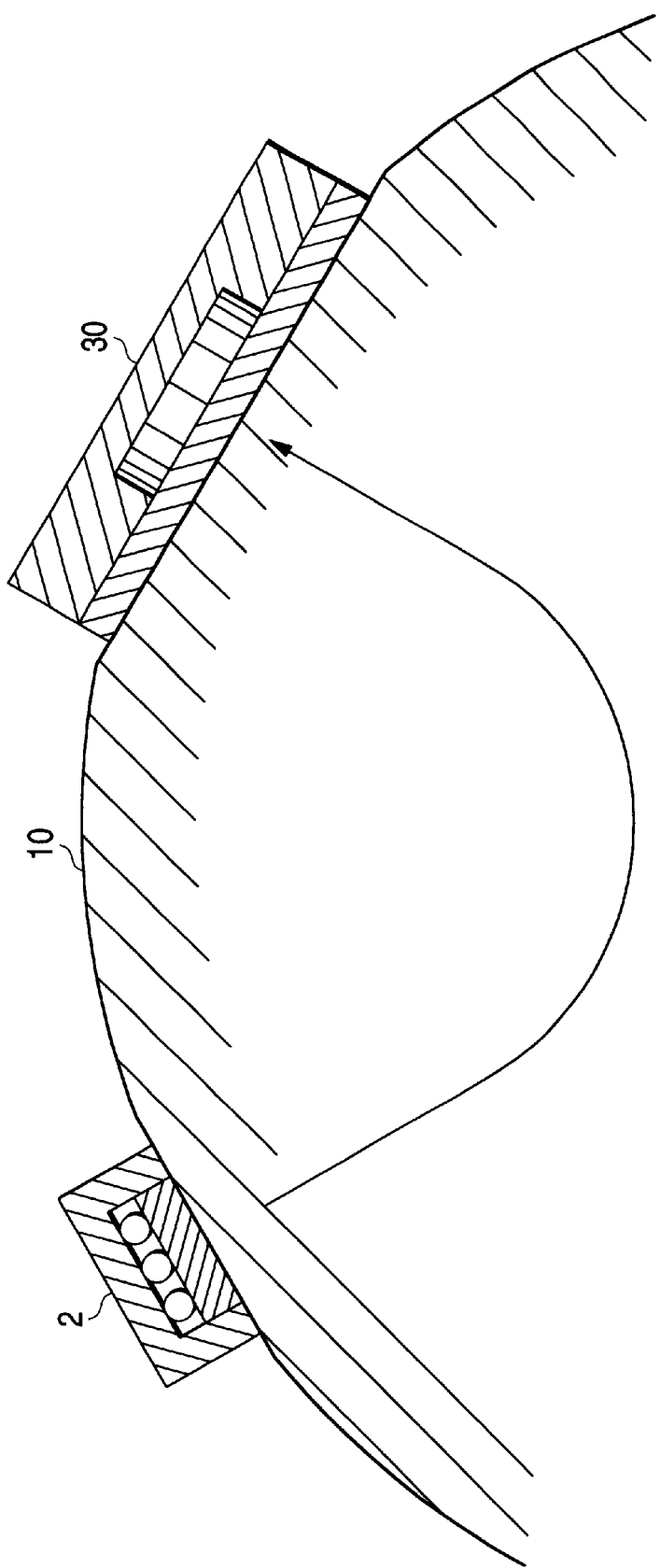
FIG. 6 is a cross sectional view showing still another probe according to the present invention, the reflection type probe with the same construction of the probe shown in FIG. 4.

The probes used in the embodiments are of the light transmission type, but it may be of the reflection type. In the probe of the reflection type, the light irradiating device 2 and the light receiving device 3 in the probe 1 illustrated in FIG. 1 are placed at two separate locations on the surface of the living tissue 10 as shown in FIG. 5, those two locations being disposed not oppositely. Alternatively, the light irradiating device 2 and the light receiving device 30 in the probe 1 shown in FIG. 4 are placed at two separate locations on the surface of the living tissue 10 as shown in FIG. 6, those two locations being disposed not oppositely. If the signals produced by the probe of this type are processed as in the processing of the transmitted lights in each embodiment mentioned above, the measurements on the oxygen saturation and the dye dilution curve may be performed in similar ways While the present invention has been described by using the measurement of the light absorbing material in the blood which utilizes a pulsation of light transmitted through living tissue, the invention may be applied to a near-infrared-rays spectro-measurement (NIRS), which is not based on the pulsation.

In the present invention, the light scattering portions are provided on both the light irradiating device and the light receiving device of the probe, and therefore, there is eliminated the influence by the non-absorbing attenuation. Where such a probe is used, a ratio of the absorbing attenuation and the thickness of the blood layer is not affected by the thickness of living tissue, and the absorbing attenuation is not dependent on the depth of the is blood layer in the living tissue. Accordingly, a measuring apparatus using such a probe is capable of noninvasively and accurately determining concentration of light-absorbing materials in living tissue by using simple equations.

The disclosures of U.S. Ser. No. 09/356,521, now U.S. Pat. No. 6,230,035, are incorporated herein by reference.

What is claimed is:

1. A probe comprising:
    a light irradiating device for irradiating living tissue with light, said light irradiating device including a light source for emitting a plurality of lights of different wavelengths;
    a first light scattering plate located in front of said light source; and
    a light receiving device for receiving light from said living tissue , said light receiving device including a photo-electric transducing portion for producing a signal based on an intensity of light received on a light sensitive surface, and a second light scattering plate located in front of said photo-electric transducing portion;
    wherein said light receiving device includes a light mixing portion provided between said second light scattering plate and said light sensitive surface.

2. A probe according to claim 1, wherein said light mixing portion includes a closed space defined by an inner light reflective wall of a housing, said second light scattering plate and the light sensitive surface.

3. A probe according to claim 1, wherein said light mixing portion is positioned between said photo-electric transducing portion and said second light scattering portion.

4. A probe according to claim 1, wherein said photo-electric transducing portion and said second light scattering portion are disposed opposite each other.

5. A probe according to claim 1, wherein said light receiving device includes a housing for accommodating said photo-electric transducing portion, and a surface of said housing contacting said second scattering plate is light reflective.

6. A probe according to claim 1, wherein said first light scattering plate and said second light scattering plate transmit light diffusively.

7. An apparatus for determining concentration of light-absorbing materials in living tissue, comprising:
  a probe comprising:
    a light irradiating device for irradiating living tissue with light, said light irradiating device including a light source for emitting a plurality of lights of different wavelengths;
    a first light scattering portion located in front of said light source; and
    a light receiving device for receiving light from said living tissue, said light receiving device including a photo-electric transducing portion for producing a signal based on an intensity of light received on a light sensitive surface, and a second light scattering portion, said light receiving device further including a light mixing portion provided between said second light scattering portion and said light sensitive surface, and concentration-ratio processing means for computing at least one ratio of concentrations of a plurality of light-absorbing materials in said living tissue based on an output signal of said photo-electric transducing portion of said probe.

8. An apparatus for determining concentration of light-absorbing materials in living tissue according to claim 7, wherein said concentration-ratio processing means obtains a variation of an optical attenuation of said living tissue based on a pulsating component of an output signal of said photo-electric transducing portion, and computes a ratio of concentrations of a plurality of light-absorbing materials based on the obtained attenuation variation.

9. An apparatus for determining concentration of light-absorbing materials in living tissue according to claim 8, wherein said concentration-ratio processing means includes:
  attenuation variation component detecting means for obtaining attenuation variation components $\Delta A1, \Delta A2, \ldots, \Delta An$ of the respective wavelengths from variations of lights transmitted through or reflected by said living tissue when said living tissue is irradiated by said light irradiating device;
  variation component ratio detecting means for obtaining a ratio $\phi ij$ of each of an "m" number of combinations of two attenuation variation components ($\Delta Ai, \Delta Aj$) selected from an "n" number of attenuation variation components $\Delta A1, \Delta A2, \ldots, \Delta An$ obtained by said attenuation variation component detecting means, and
  computing means for computing at least one of an oxygen saturation and a ratio of concentrations of light-absorbing materials in blood based upon an "m" number of simultaneous equations about said respective wavelengths and an "m" number of ratios $\phi ij$ obtained by said variation component ratio detecting means, on the assumption that said attenuation variation component is the sum of the attenuation variation components of absorbing attenuation and non-absorbing attenuation.

10. An apparatus for determining concentration of light-absorbing materials in living tissue according to claims 7, wherein said first light scattering portion includes a first light scattering plate, and second light scattering portion includes a second light scattering plate.

11. An apparatus for determining concentration of light-absorbing materials in living tissue according to claim 7, wherein said light mixing portion includes a closed space defined by an inner light reflective wall of a housing, said second light scattering portion and the light sensitive surface.

12. An apparatus for determining concentration of light-absorbing materials in living tissue according to claim 7, wherein said light receiving device includes a housing for accommodating said photo-electric transducing portion, and a surface of said housing contacting said second scattering portion is light reflective.

* * * * *